(12) United States Patent
Jung et al.

(10) Patent No.: US 7,435,759 B2
(45) Date of Patent: Oct. 14, 2008

(54) METHOD FOR THE PRODUCTION OF DIMETHYL ETHER

(75) Inventors: Kwang-Deog Jung, Seoul (KR); Oh-Shim Joo, Seoul (KR); Jun-Woo Oh, Seoul (KR)

(73) Assignee: Korea Institute of Science and Technology (KR)

( * ) Notice: Subject to any disclaimer, the term of this patent is extended or adjusted under 35 U.S.C. 154(b) by 214 days.

(21) Appl. No.: 10/571,867

(22) PCT Filed: Jan. 29, 2004

(86) PCT No.: PCT/KR2004/000156

§ 371 (c)(1),
(2), (4) Date: Mar. 14, 2006

(87) PCT Pub. No.: WO2005/026093

PCT Pub. Date: Mar. 24, 2005

(65) Prior Publication Data

US 2007/0142482 A1    Jun. 21, 2007

(30) Foreign Application Priority Data

Sep. 17, 2003    (KR) .................. 10-2003-0064296

(51) Int. Cl.
*C07C 27/00* (2006.01)

(52) U.S. Cl. ............... 518/700; 518/713; 518/714; 518/726; 502/307; 502/325; 502/342

(58) Field of Classification Search ........... 518/700, 518/713, 714, 726; 502/307, 325, 342
See application file for complete search history.

(56) References Cited

U.S. PATENT DOCUMENTS

| 4,098,809 A | * | 7/1978 | Pagani ................. 518/713 |
| 2003/0113244 A1 | * | 6/2003 | Dupont et al. ............. 422/211 |
| 2003/0162846 A1 | * | 8/2003 | Wang et al. ................ 518/703 |

OTHER PUBLICATIONS

O.V.Krylov, A.Kh.Mamedov, S.R.Mirzabekova; Interaction of carbon dioxide with methane on oxide catalysts; Catalysis Today, 1998, 42, 211-215.*

* cited by examiner

*Primary Examiner*—Yvonne Eyler
*Assistant Examiner*—Sudhakar Katakam
(74) *Attorney, Agent, or Firm*—Baker & Hoestetler, LLP

(57) ABSTRACT

A method for producing DME, which comprises separating a $CO_2$ rich stream from a crude product stream containing DME and $CO_2$ obtained by a DME synthesis from a feed syn gas; introducing the $CO_2$ rich stream to a reverse water gas shift (RWGS) reactor wherein it is reacted with hydrogen in the presence of an oxide catalyst of either ZnO or NiO to provide a CO rich stream, and recycling the CO rich stream to the step of the methanol synthesis step.

6 Claims, 1 Drawing Sheet

METHOD FOR THE PRODUCTION OF DIMETHYL ETHER

FIELD OF THE INVENTION

The present invention relates to a method for producing dimethyl ether in a high yield, by way of exploiting the reverse water gas shift reaction to effectively re-use carbon dioxide generated during the direct methanol synthesis process.

BACKGROUND ART

Dimethyl ether (DME) has been prepared by a direct synthesis method, wherein a synthesis gas ($CO/H_2$) is directly converted to dimethyl ether in the presence of a methanol synthesis catalyst and a catalyst for the dehydration of methanol (see K. Fujimoto et al., Chemistry Letters, pp 2051-2054). Many studies have been made to improve the performances of the catalysts used in this synthesis method (see U.S. Pat. Nos. 4,098,809; 4,375,424; 4,417,000; and 4,590,176).

In the direct methanol synthesis method, three reactions proceed simultaneously, i.e., the methanol synthesis, the dehydration of methanol to give DME, and the water gas shift reaction, as shown in Reaction Schemes A, B and C.

$$CO + 2H_2 \rightleftharpoons CH_3OH$$

$$2CH_3OH \rightleftharpoons CH_3OCH_3 + H_2O$$

$$CO + H_2O \rightleftharpoons CO_2 + H_2$$

Consequently, an integration of the above three reactions is represented by Reaction Scheme D.

$$3CO + 3H_2 \rightleftharpoons CH_3OCH_3 + CO_2$$

As shown above, most of water generated in the course of the dehydration of methanol for the production of DME is converted to carbon dioxide by the water gas shift reaction. As a result, the production of DME is accompanied by the generation of a 1 mole equivalent amount of carbon dioxide, which causes a green house effect.

SUMMARY OF THE INVENTION

Accordingly, it is an object of the present invention to provide a novel method for the production of DME in a high yield with a reduced amount of carbon dioxide generated.

In accordance with one aspect of the present invention, there is provided a method for producing DME, which comprises the steps of:
(i) introducing a feed gas mixture of hydrogen and CO to a DME synthesis reactor, wherein the feed gas mixture is reacted in the presence of a methanol synthesis catalyst and an acid catalyst for the dehydration of methanol to provide a crude product stream containing DME and $CO_2$;
(ii) separating the crude product stream into a $CO_2$ rich stream and a DME rich stream;
(iii) introducing the $CO_2$ rich stream to a reverse water gas shift (RWGS) reactor, wherein it is reacted with hydrogen in the presence of a catalyst to convert $CO_2$ into CO, while recovering the DME rich stream as a product; and (iv) recycling the CO and $H_2$ rich stream to step (i).

BRIEF DESCRIPTION OF THE DRAWINGS

The above and other objects and features of the present invention will become apparent from the following description of the invention, when taken in conjunction with the accompanying drawing which shows.

DETAILED DESCRIPTION OF THE INVENTION

Figure 1:
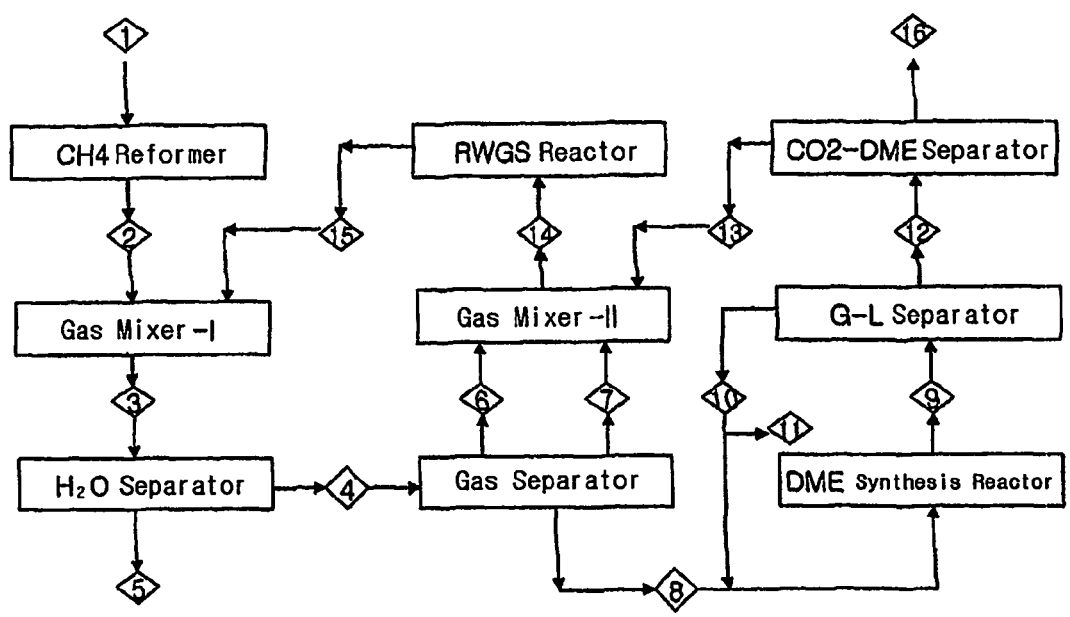
FIG. 1: a schematic block diagram for one embodiment of the DME production process according to the present invention.

The inventive method is characterized in that a large amount of carbon dioxide gas generated in the course of the production of DME is converted back to carbon monoxide by the reverse water gas shift (RWGS) reaction, and said carbon monoxide is recycled to the DME production process, thus increasing the yield of DME.

Synthesis of DME

The DME synthesis reaction of a feed gas containing hydrogen and carbon monoxide according to the present invention is conducted in the presence of a mixture of a catalyst for methanol synthesis and a catalyst for the hydration of methanol thus produced, in a fixed bed or slurry reactor.

The catalyst for the methanol synthesis may be typically a Cu-based three- or four-component catalyst, e.g., $Cu/ZnO/Ga_2O_3/Al_2O_3$, which is commercially available.

Further, the catalyst for the hydration of methanol may be a solid acid including alumina, γ-alumina, zeolite, and a mixture thereof.

The mixed catalyst used in the DME synthesis process may comprise 0.01 to 80% by weight, preferably 0.02 to 60% by weight of the acid catalyst, and the remaining amount of the methanol synthesis catalyst.

The DME synthesis reaction may be conducted by introducing the feed gas at a flow rate of 500 to 50,000 $mL/g_{cat} \cdot h$ at a temperature ranging from 160 to 400° C., preferably 180 to 350° C. under a pressure ranging from 20 to 200 atm, preferably 30 to 100 atm, to provide a crude product stream containing DME, $CO_2$ and others.

The crude product stream is then separated into a $CO_2$ rich stream and a DME rich stream, and the DME rich stream is recovered as a product, while the $CO_2$ rich stream is introduced to a reverse water gas shift (RWGS) reactor to be subjected to the RWGS reaction.

RWGS Reaction

In the RWGS reactor, the $CO_2$ rich stream is reacted with hydrogen in the presence of a catalyst to provide a CO rich stream. The RWGS reaction shown below may be preferably carried out, in the presence of an oxide catalyst, at a temperature ranging from 400 to 1,200° C., preferably from 500 to 1,000° C., under a pressure ranging from 1 to 100 atm, preferably from 1 to 20 atm.

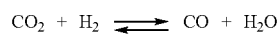

$$CO_2 + H_2 \rightleftharpoons CO + H_2O$$

The catalyst which may be used in the present invention includes a composite oxide catalyst selected from the group consisting of:

1) ZnO supported on or co-precipitated with an oxide selected from $Cr_2O_3$, $Al_2O_3$, $ZrO_2$, MgO, MnO, $SiO_2$ and a mixture thereof, the content of ZnO being 10 to 90% by weight based on the total weight of the catalyst;

2) $MnO_x$ (x=1~2) supported on or co-precipitated with an oxide selected from $Cr_2O_3$, $Al_2O_3$, $ZrO_2$, MgO, $SiO_2$ and a mixture thereof, the content of $MnO_x$, being 1 to 99% by weight, preferably 1 to 40% by weight based on the total weight of the catalyst;

3) an alkaline earth metal oxide (e.g., CaO, BaO, and MgO) supported on or co-precipitated with an oxide selected from $Cr_2O_3$, $Al_2O_3$, $ZrO_2$, MnO, $SiO_2$ and a mixture thereof, the content of alkaline earth metal oxide being 1 to 99% by weight, preferably 1 to 40% by weight based on the total weight of the catalyst; and 4) NiO supported on or co-precipitated with an oxide selected from $Cr_2O_3$, $Al_2O_3$, $ZrO_2$, MgO, $SiO_2$ and a mixture thereof, the content of NiO being 1 to 20% by weight, preferably 1 to 10% by weight based on the total weight of the catalyst.

The composite oxide catalyst may have a spinel structure, and the supporting or co-precipitating method can be carried out in a conventional manner. For example, a supported catalyst may be prepared by impregnating a support material with an aqueous or organic solution containing a soluble salt of the desired element, e.g., a chloride, nitrate or sulfate, drying and calcining the impregnated support material. Further, a co-precipitated catalyst may be prepared by adding a precipitating agent to an aqueous solution containing a soluble salt of the active metal element to form precipitates, and aging, drying and calcining the precipitates thus produced. The resultant catalyst may be in the form of powders, pellets or granules.

When the content of the catalytically active material (i.e., ZnO, MnOx, alkaline earth metal oxide, or NiO) in the catalyst is less than the lower limit, the activity of the catalyst is low, whereas when the content exceeds the upper limit, the catalyst can be deactivated.

The above-mentioned ZnO catalyst may further comprise a Cu or Mn-based component in an amount of 0.01 to 60% by weight, preferably 0.01 to 10% by weight based on the total weight of the catalyst. Further, particularly preferred catalyst among the alkaline earth metal oxide containing catalysts is a hexa-aluminate comprised of BaO, MgO and $Al_2O_3$.

In the inventive method, the CO rich stream produced by the RWGS reaction is recycled to control the ratio of hydrogen and CO in the feeding gas for the DME synthesis reaction, thereby rendering the total yield of the DME synthesis reaction to be increased. The controlled molar ratio of hydrogen to CO in the feeding gas for the DME synthesis may preferably range from 0.8 to 2.5. Because a feeding gas for the methanol synthesis is conventionally derived from the refinery process of methane which generates an excessive amount of hydrogen, the CO rich stream produced in the reverse water gas reaction can be beneficially used in the control of the molar ratio of the feeding gas, and therefore, the productivity of DME according to the present invention is very high.

One example of embodiments of the new DME synthesis process including RWGS reactor according to the present invention is shown in FIG. 1. Specifically, at first, methane (1) is reacted with oxygen in a methane reformer to provide a mixed gas stream (2) containing hydrogen and water. In gas mixer-I, the gas stream (2) is combined with gas stream (15) containing CO and hydrogen, which is produced by a RWGS reaction from carbon dioxide generated during DME synthesis reaction. The combined gas stream (3) is introduced to a water separator, wherein water (5) is removed while the remaining gas stream (4) is led to a gas separator (amine absorber/PSA or 3 way PSA separator) to be separated into three streams, i.e., $H_2$ rich stream (6), $CO_2$ rich stream (7) and feed gas stream (8).

The feeding gas stream (8) is then combined with stream (10) containing $H_2$ and $CO_2$ separated from the reaction product of the DME synthesis reaction to adjust the molar ratio of $H_2$/CO thereof to about 0.9 to 1.5, and the adjusted feeding gas is led to the DME synthesis reactor.

On the other hand, both streams (6) and (7) are introduced to gas mixer-II, wherein they are combined with $CO_2$-rich stream (13) obtained from the $CO_2$-DME separator, to provide gas stream (14) containing $CO_2$ and $H_2$ for RWGS reaction. The gas stream (14) is subsequently sent to the RWGS reactor to convert $CO_2$ present therein to CO, thus providing the CO and $H_2$ containing stream (15).

In the DME synthesis reactor, the feed gas stream is reacted in the presence of a methanol synthesis catalyst and a methanol dehydration catalyst to produce crude product stream (9) containing CO, $H_2$, $CO_2$, DME, $CH_3OH$ and others. The crude product stream (9) is then introduced to a gas-liquid separator (G-L separator) to be separated into a stream (10), and a stream (12). The stream (10) is then recycled to be combined with a feed gas for DME synthesis, as mentioned previously. The stream (12), on the other hand, is introduced to a $CO_2$-DME separator to be separated into a $CO_2$ rich stream (13) and a DME rich stream (16), the stream (13) being introduced to the gas mixer-II while the stream (16) being recovered as a product.

In accordance with the present invention, a large amount of carbon dioxide gas generated during the production of DME can be re-used by a reverse water gas shift reaction, thus increasing the yield of DME.

The following Examples are given for the purpose of illustration only, and are not intended to limit the scope of the invention.

RWGS Reaction

REFERENCE EXAMPLE 1

$NiAl_2O_4$ was prepared by a conventional co-precipitation method. Specifically, 0.3 mole of Ni nitrate and 0.6 mole of Al nitrate salt were dissolved in 500 mL of the distilled water. 0.1 mole of NaOH aqueous solution was added into the aqueous metal salt solution to co-precipitate Al and Ni components. The precipitate was filtered, washed and dried. The dried sample was calcined at 850° C. for 3 hours.

0.5 g of $NiAl_2O_4$ was charged into a ⅜" fixed bed reactor using a quartz wool support. The reactor was maintained at an ambient pressure, and a mixture of carbon dioxide and hydrogen having a molar ratio of 1:3 was fed to the reactor at a flow rate of 24,000 cm³/h.g$_{cat}$ to carry out the reverse water gas reaction at a temperature in the range of 500 to 900° C. The $CO_2$ conversion, CO selectivity and $CH_4$ selectivity were determined as follows.

$CO_2$ conversion=(moles of $CO_2$ injected−moles of $CO_2$ consumed during the reaction)×100/(moles of $CO_2$ injected)

CO selectivity=moles of CO generated×100/moles of CO converted $CH_4$ selectivity=moles of $CH_4$ generated×100/moles of $CH_4$ converted The results of the measurement are shown in Table 1.

TABLE 1

| | Reaction Temperature (° C.) | | | | | | | | |
|---|---|---|---|---|---|---|---|---|---|
| | 500 | 550 | 600 | 650 | 700 | 750 | 800 | 850 | 900 |
| $CO_2$ conversion | 54.9 | 57.7 | 58.7 | 63.2 | 67.5 | 70.8 | 73.2 | 75.8 | 78.3 |
| CO selectivity | 11.3 | 16.9 | 32.4 | 49.1 | 62.8 | 69.2 | 72.6 | 75.8 | 78.3 |
| $CH_4$ selectivity | 43.6 | 40.8 | 26.3 | 14.1 | 4.7 | 1.6 | 0.6 | — | — |

REFERENCE EXAMPLE 2

The procedure of Reference Example 1 was repeated except that a mixture having a molar ratio of carbon dioxide and hydrogen of 1:1 was used, and the results are shown in Table 2.

TABLE 2

| | Reaction Temperature (° C.) | | | | | | | | |
|---|---|---|---|---|---|---|---|---|---|
| | 500 | 550 | 600 | 650 | 700 | 750 | 800 | 850 | 900 |
| $CO_2$ conversion | 28.2 | 30.9 | 35.9 | 40.5 | 44.1 | 46.7 | 49.4 | 51.0 | 52.9 |
| CO selectivity | 16.0 | 21.7 | 31.1 | 39.2 | 43.9 | 46.7 | 49.4 | 51.0 | 52.9 |
| $CH_4$ selectivity | 12.2 | 9.2 | 4.8 | 1.3 | 0.2 | — | — | — | — |

REFERENCE EXAMPLE 3

$ZnAl_2O_4$ was prepared by a conventional co-precipitation method. Specifically, 29.75 g of Zn nitrate and 75.02 g of Al nitrate were dissolved in 250 mL of the distilled water. 0.1 mole of NaOH aqueous solution was added into the aqueous metal salt solution to co-precipitate Al and Zn components. The precipitate was filtered, washed and dried. The dried sample was calcined at 850° C. for 3 hours. The calcined catalyst was impregnated with copper nitrate and then calcined at 450° C. for 3 hours to obtain $Cu(0.5\%)/ZnAl_2O_4$.

0.5 g of the catalyst was charged into a ⅜" fixed bed reactor using a quartz wool support. A mixed gas having a molar ratio of carbon dioxide and hydrogen of 1:3 was fed to the reactor maintained at an ambient pressure at a GHSV of 40,000 cm³/h·$g_{cat}$, to carry out the reverse water gas reaction at a temperature in the range of 500 to 900° C. The $CO_2$ conversion rate was measured as mentioned above, and the results are shown in Table 3.

TABLE 3

| | Reaction Temperature (° C.) | | | | | | | | |
|---|---|---|---|---|---|---|---|---|---|
| | 500 | 550 | 600 | 650 | 700 | 750 | 800 | 850 | 900 |
| $CO_2$ conversion rate | 49.1 | 55.6 | 60.3 | 65.5 | 68.9 | 72.9 | 74.5 | 76.4 | 79.8 |

REFERENCE EXAMPLE 4

The procedure of Reference Example 3 was repeated except that the reverse water gas reaction was conducted at 600° C. and 150,000 cm³/h·$g_{cat}$ to follow the time-dependent charges, and the results are shown in Table 4.

TABLE 4

| | Reaction Time (hr) | | | | | | | |
|---|---|---|---|---|---|---|---|---|
| | 1 | 24 | 48 | 72 | 96 | 120 | 144 | 168 |
| $CO_2$ conversion rate | 30.2 | 31.2 | 29.9 | 31.0 | 30.7 | 31.2 | 31.6 | 31.3 |

REFERENCE EXAMPLE 5

The procedure of Reference Example 3 wash repeated except that a $ZnO/MnO_2$ catalyst prepared by a co-precipitation method was employed, and the results are shown in Table 5.

TABLE 5

| | Reaction Temperature (° C.) | | | | | | | | |
|---|---|---|---|---|---|---|---|---|---|
| | 500 | 550 | 600 | 650 | 700 | 750 | 800 | 850 | 900 |
| $CO_2$ conversion rate | 48.9 | 54.6 | 60.1 | 65.1 | 68.2 | 71.9 | 74.3 | 77.4 | 79.6 |

REFERENCE EXAMPLE 6

The procedure of Reference Example 3 was repeated except that the reverse water gas reaction was conducted at 600° C. for 210 hours while the reaction pressure was varied from 1 to 50 atm. The change in the $CO_2$ conversion rate was measured as mentioned above, and the results are shown in Table 6.

TABLE 6

| | Reaction Pressure (atm) | | | | | |
|---|---|---|---|---|---|---|
| | 1 | 10 | 20 | 30 | 40 | 50 |
| $CO_2$ conversion rate | 59.6 | 60.3 | 60.5 | 60.8 | 60.9 | 60.3 |

DME Synthesis

DME was produced from methane, in accordance with the process as shown in FIG. 1. In the DME synthesis reaction, the $H_2$/CO molar ratio of the feed gas was maintained at 1.2 and a 2:8 (by weight) mixture of ICI-54 ($Cu/ZnO/Al_2O_3$(6:3:1)) and alumina was employed as a catalyst. Further, the catalyst used in the RWGS reaction was the same as prepared in Reference Example 3.

In the final product stream, 92.6 mole % DME was obtained at a yield of 92.4%.

The partial mole ratios of the stream obtained in the respective step are listed in Table 7.

TABLE 7a

| | Stream | | | | | | |
|---|---|---|---|---|---|---|---|
| | 2 | 3 | 4 | 6 | 7 | 8 | 9 |
| Temp. (° C.) | 535 | 50 | — | 50 | 50 | 280 | −10 |
| Pressure (kg/cm³) | 6.03 | 6.03 | — | 51.03 | 51.03 | 51.03 | 51.03 |
| $H_2$ (molar ratio) | 0.3398794 | 0.4570792 | 0.6815813 | 0.9982770 | — | 0.482914 | 0.2437937 |
| CO (molar ratio) | 0.0813524 | 0.1153308 | 0.1719775 | 0.0017200 | 0.0127427 | 0.401153 | 0.1383429 |
| $CO_2$ (molar ratio) | 0.0770776 | 0.0867334 | 0.1293239 | — | 0.8624092 | 0.010484 | 0.3725413 |
| $CH_4$ (molar ratio) | 0.0000639 | 0.0000846 | 0.000126 | — | — | 0.001300 | 0.0020500 |
| $N_2$ (molar ratio) | 0.0001210 | 0.0000999 | 0.000149 | — | 0.0000552 | 0.001950 | 0.0035300 |
| $H_2O$ (molar ratio) | 0.5015053 | 0.3406696 | 0.0168385 | — | 0.1247664 | 0.000066 | 0.0137824 |
| DME (molar ratio) | — | — | 0.0000036 | — | 0.0000264 | 0.007930 | 0.2103037 |
| MeOH (molar ratio) | — | — | — | — | — | 0.000023 | 0.0156575 |
| Total flow (kmol/h) | 7.161153 | 13.86761 | 9.299532 | 4.640273 | 1.255073 | 4.691872 | 2.5851780 |

TABLE 7b

| | Stream | | | | | | |
|---|---|---|---|---|---|---|---|
| | 10 | 11 | 12 | 13 | 14 | 15 | 16 |
| Temp. (° C.) | −10 | −10 | −12 | −23 | 650 | 650 | 74 |
| Pressure (kg/cm³) | 51.03 | 51.03 | 21 | 19 | 7.03 | 7.03 | 19.33 |
| $H_2$ (molar ratio) | 0.434625 | 0.434625 | 0.007430 | 0.015024 | 0.7278002 | 0.582234 | — |
| CO (molar ratio) | 0.238286 | 0.238286 | 0.014358 | 0.029032 | 0.0060500 | 0.151615 | — |
| $CO_2$ (molar ratio) | 0.288619 | 0.288619 | 0.476520 | 0.953906 | 0.2426112 | 0.097044 | 0.009430 |
| $CH_4$ (molar ratio) | 0.003200 | 0.003200 | 0.000619 | 0.001250 | 0.000107 | 0.000107 | — |
| $N_2$ (molar ratio) | 0.006070 | 0.006070 | 0.000388 | 0.000785 | 0.0000772 | 0.000077 | — |
| $H_2O$ (molar ratio) | 0.000242 | 0.000242 | 0.030564 | — | 0.0233512 | 0.168913 | 0.060470 |
| DME (molar ratio) | 0.028876 | 0.028876 | 0.435162 | — | 0.0000050 | 0.000005 | 0.860939 |
| MeOH (molar ratio) | 0.000084 | 0.000084 | 0.034959 | — | — | — | 0.069164 |
| Total flow (kmol/h) | 1.430736 | 0.143076 | 1.1554422 | 0.570920 | 6.706009 | 6.706009 | 0.583503 |

As shown in Tables 7a and 7b, the content of carbon dioxide gas to be discharged in the inventive method is insignificant as compared with the amount of DME produced.

In accordance with the present invention, a large amount of carbon dioxide gas generated during the manufacturing process of DME is effectively re-used via the reverse water gas reaction, thus increasing the yield of DME and lowering the amount of carbon dioxide discharged. Further, since the DME product stream obtained in the inventive method contains less than 20 by weight of methanol and less than 20% by weight of water, it has an advantage that it can be directly used as a fuel.

While the invention has been described with respect to the above specific embodiments, it should be recognized that various modifications and changes may be made to the invention by those skilled in the art which also fall within the scope of the invention as defined by the appended claims.

The invention claimed is:

1. A method for producing dimethylether (DME), which comprises the steps of:

(i) introducing a feed gas mixture containing hydrogen and CO to a DME synthesis reactor, wherein the feed gas mixture is reacted in the presence of a methanol synthesis catalyst and an acid catalyst for the dehydration of methanol, to provide a crude product stream containing DME and $CO_2$;

(ii) separating the crude product stream into a $CO_2$ rich stream and a DME rich stream;

(iii) introducing the $CO_2$ rich stream to a reverse water gas shift (RWGS) reactor wherein it is reacted with hydrogen separately introduced in the presence of an oxide catalyst to provide a CO rich stream, while recovering the DME rich stream as a product, the oxide catalyst being ZnO supported on or coprecipitated with an oxide selected from $Al_2O_3$, $ZrO_2$, MgO, $SiO_2$ and a mixture thereof and the reaction in the reverse water gas reactor being carried out at a temperature ranging from 500 to 900° C.; and (iv) recycling the CO rich stream to step (i).

2. The method of claim 1, wherein the content of ZnO in the ZnO catalyst ranges from 10 to 90% by weight based on the total weight of the catalyst.

3. The method of claim 1, wherein the ZnO catalyst further comprises an oxide of Cu or Mn in an amount of 0.01 to 60% by weight based on the total weight of the catalyst.

4. A method for producing dimethylether (DME), which comprises the steps of:

(i) introducing a feed gas mixture containing hydrogen and CO to a DME synthesis reactor, wherein the feed gas mixture is reacted in the presence of a methanol synthesis catalyst and an acid catalyst for the dehydration of methanol, to provide a crude product stream containing DME and $CO_2$;

(ii) separating the crude product stream into a $CO_2$ rich stream and a DME rich stream;

(iii) introducing the $CO_2$ rich stream to a reverse water gas shift (RWGS) reactor wherein it is reacted with hydrogen separately introduced in the presence of an oxide catalyst to provide a CO rich stream, while recovering the DME rich stream as a product, the oxide catalyst being NiO supported on or coprecipitated with an oxide selected from $Al_2O_3$, $ZrO_2$, MgO, $SiO_2$ and a mixture thereof, and the reaction in the reverse water gas reactor being carried out at a temperature ranging from 700 to 900° C.; and (iv) recycling the CO rich stream to step (i).

5. The method of claim 1, wherein the molar ratio of hydrogen and CO in step (iv) is controlled to 0.9~1.5:1.

6. The method of claim 4, wherein the content of NiO in the NiO catalyst ranges from 1 to 20% by weight based on the total weight of the catalyst.

* * * * *